(12) United States Patent
Storment

(10) Patent No.: US 8,268,382 B2
(45) Date of Patent: Sep. 18, 2012

(54) METHOD OF MAKING A STENT WITH HOLLOW STRUTS

(75) Inventor: Christopher Storment, Sonoma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 333 days.

(21) Appl. No.: 12/834,274

(22) Filed: Jul. 12, 2010

(65) Prior Publication Data
US 2012/0009325 A1 Jan. 12, 2012

(51) Int. Cl.
*A61F 2/02* (2006.01)
*A61F 2/82* (2006.01)
*B05D 5/00* (2006.01)
*C25D 1/08* (2006.01)

(52) U.S. Cl. ....... 427/2.25; 205/75; 623/23.7; 623/1.42; 424/423

(58) Field of Classification Search ................. 427/2.25; 205/75; 623/23.7, 1.42; 424/423
See application file for complete search history.

(56) References Cited

U.S. PATENT DOCUMENTS

| | | | |
|---|---|---|---|
| 4,739,762 A | 4/1988 | Palmaz | |
| 5,421,955 A | 6/1995 | Lau | |
| 6,090,127 A | 7/2000 | Globerman | |
| 6,379,383 B1 | 4/2002 | Palmaz et al. | |
| 2003/0159920 A1 | 8/2003 | Roth | |
| 2004/0024449 A1 | 2/2004 | Boyle | |
| 2008/0195170 A1 | 8/2008 | Asgari | |
| 2010/0145437 A1* | 6/2010 | Girton et al. | 623/1.42 |

* cited by examiner

*Primary Examiner* — Timothy Vanoy

(57) ABSTRACT

A stent including hollow struts is formed on a cylindrical substrate. The struts of the stent are formed by electroforming metal layers of the strut in openings formed in a patterned photoresist material. A first metal layer forming the inner strut material is formed in openings in a first photoresist material. A sacrificial material to form the cavity to make the struts hollow is formed in openings in a second photoresist material. A second metal layer forming the side walls and outer wall of the struts is formed in openings in a third photoresist material and around the sacrificial material. The photoresist materials are removed. The substrate and cavity sacrificial material are removed, leaving hollow struts formed into a stent pattern. The hollow struts may be filled with a therapeutic substance for elution. Openings through the struts to the cavity may be formed during the forming process.

12 Claims, 5 Drawing Sheets

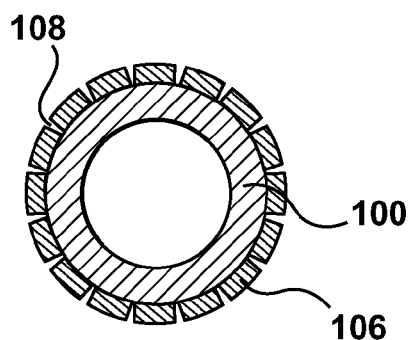 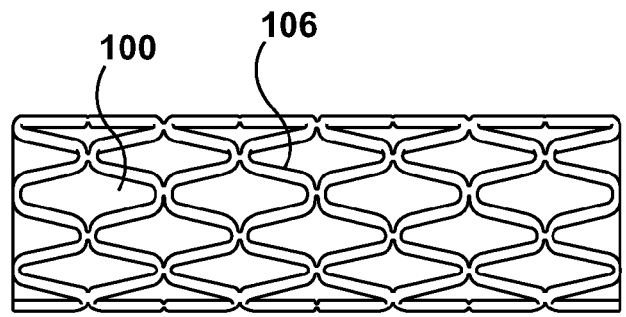
FIG. 5   FIG. 5A
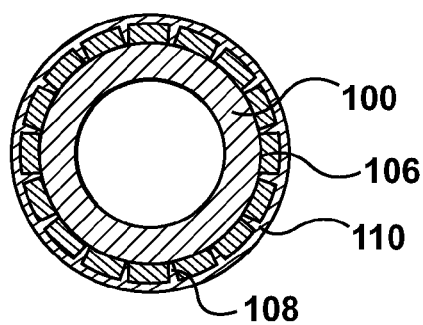 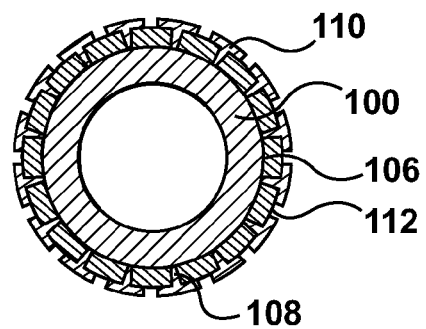
FIG. 6   FIG. 7
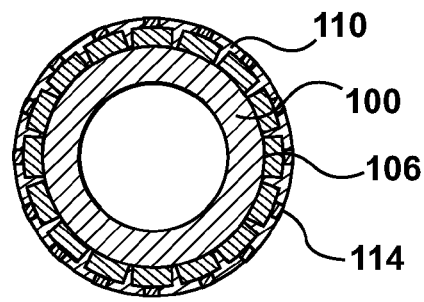
FIG. 8

METHOD OF MAKING A STENT WITH HOLLOW STRUTS

FIELD OF THE INVENTION

The present invention relates to implantable medical devices that release a therapeutic substance and methods of forming such medical devices.

BACKGROUND OF THE INVENTION

Drug-eluting implantable medical devices have become popular in recent times for their ability to perform their primary function (such as structural support) and their ability to medically treat the area in which they are implanted.

For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical stents may be coated with a polymeric material which, in turn, is impregnated with a drug or a combination of drugs. Once the stent is implanted at a target location, the drug is released from the polymer for treatment of the local tissues. The drug is released by a process of diffusion through the polymer layer for biostable polymers, and/or as the polymer material degrades for biodegradable polymers.

Controlling the rate of elution of a drug from the drug impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the drug from reaching the target site. Still further, drug impregnated polymer coatings are limited in the quantity of the drug to be delivered by the amount of a drug that the polymer coating can carry and the size of the medical devices. Controlling the rate of elution using polymer coatings is also difficult.

Stents made from a hollow-tubular wire filled with therapeutic agents have been proposed. However, forming a hollow-wire stent by bending a hollow-wire into a stent form may cause kinking, cracking, or other undesirable properties in the finished stent. Thus, it would be desirable to make a drug-eluting stent with hollow struts without bending a wire into a stent shape.

BRIEF SUMMARY OF THE INVENTION

An embodiment of a method of making a stent including hollow struts includes depositing a first photoresist layer on a substantially cylindrical substrate. The substrate is at least partially made from a sacrificial material. The first photoresist layer is patterned to provide openings in the first photoresist layer. A first metal layer is then deposited on the substrate in the openings of the patterned first photoresist layer. The first photoresist layer is removed and a second photoresist layer is deposited over the first metal layer. The second photoresist layer is patterned to provide openings in the second photoresist layer, wherein the openings in the second photoresist layer are provided over the first metal layer. A sacrificial material is deposited on the first metal layer in the openings of the second patterned photoresist layer. The second photoresist layer is removed and a third photoresist layer is deposited over the sacrificial material and the first metal layer. The third photoresist layer is patterned to provide openings in the third photoresist layer. A second metal layer is deposited in the openings of the patterned third photoresist layer. The third photoresist layer is removed. The substrate and sacrificial material are removed, leaving the metal layers with a cavity formed therein. The metal layers are deposited in a pattern to form the struts of a stent.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 5 is a cross-sectional view showing that the remaining photoresist of FIG. 4 has been removed.

FIG. 6 is a cross-sectional view showing a second photoresist layer deposited over the substrate and first strut layer.

FIG. 7 is a cross-sectional view showing patterning of the second photoresist layer of FIG. 6.

FIG. 8 is a cross-sectional view showing a sacrificial material deposited in the openings of the patterned second photoresist layer of FIG. 7.

DETAILED DESCRIPTION OF THE INVENTION

Specific embodiments of the present invention are now described with reference to the figures, where like reference numbers indicate identical or functionally similar elements.

An embodiment of a method of making a stent 130 is shown in FIGS. 1-16. An example of the stent 130 is shown in FIG. 14A. However, the stent may be formed in any pattern suitable for use as a stent. For example, and not by way of limitation, stent patterns shown in U.S. Pat. No. 6,090,127 to Globerman, U.S. Pat. No. 4,739,762 to Palmaz and U.S. Pat. No. 5,421,955 to Lau, may be used.

Figure 1:
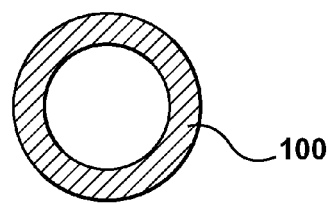
FIG. 1 is a cross-sectional view of a cylindrical substrate.

FIG. 1 is a cross-sectional view of a substrate 100. Substrate 100 in this embodiment is a cylindrical tube. Substrate 100 may be a cylindrical rod or it may be another shape matching the final overall shape of the stent. For example, and not by way of limitation, substrate 100 may be an elliptical tube or rod. Substrate 100 is made from or coated with a sacrificial material that may be removed when the stent formation process is completed, as will be explained in more detail below. Examples of suitable sacrificial materials for substrate 100 include, but are not limited to, copper, tungsten, iron, zinc, silver, aluminum, magnesium, tantalum, molybdenum, carbon (graphitic), or other suitable materials known to those of ordinary skill in the art. The sacrificial material of substrate 100 is different than the material of the final stent structure, as will be explained in more detail below.

Figure 2:
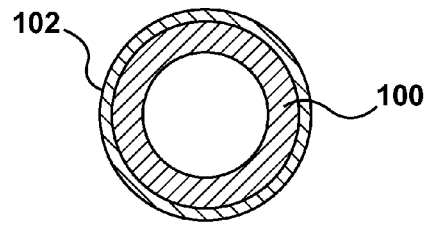
FIG. 2 is a cross-sectional view showing a photoresist layer disposed on the cylindrical substrate of FIG. 1.

The substrate 100 is coated with a first photo resistant coating layer 102 (hereinafter referred to as a "photoresist layer"), as shown in FIG. 2. First photoresist layer 102 is a light-sensitive material used to form a patterned coating on a surface, as would be understood by those of ordinary skill in the art. First photoresist layer 102 may be a positive resist or a negative resist. Photoresist layer 102 may be, for example and not by way of limitation, positive working thick film photoresists from AZ Electronic Materials (such as their 4000 and 9000 series resist resins) or SIPR® 7110M-18 available from Shin-Etsu Chemical Co., Ltd., or negative working photoresist thick films such as Micro-Chem's SU-8 series resins also are well developed for thick film applications. Photoresist layer 102 may be spray-coated onto substrate 100, or applied by other methods known to those of ordinary skill in the art. First photoresist layer 102 may be in the range of 10 to 100 microns (25-50 microns typical) in thickness.

Figure 3:
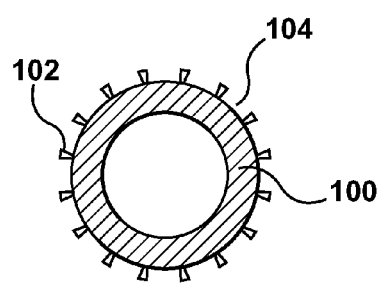
FIG. 3 is a cross-sectional view showing a portion of the photoresist layer of FIG. 2 removed.
Figure 3A:
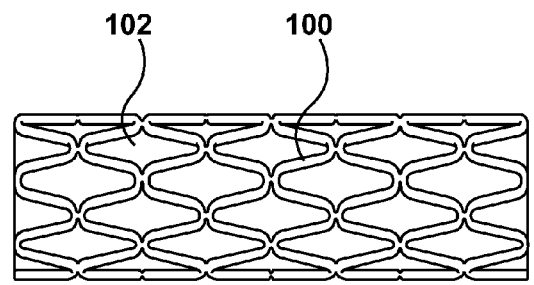
FIG. 3A is a schematic side-view of FIG. 3.
Figure 4:
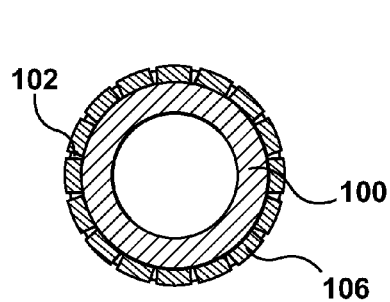
FIG. 4 is a cross-sectional view showing a first strut layer deposited in openings between the photoresist layer of FIG. 3.
Figure 4A:
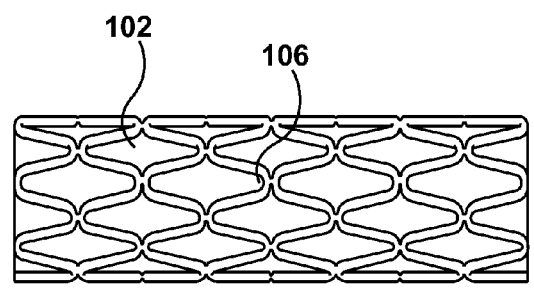

The first photoresist layer 102 is then patterned, as shown in FIGS. 3 and 3A. The photoresist layer is patterned by applying a mask to the first photoresist layer 102. The mask in this embodiment may be a tubular mask or a mask may be applied by a laser scanner. The mask includes a pattern that covers a portion of the first photoresist layer 102 and leaves a portion of the first photoresist layer 102 exposed. The first photoresist layer 102 is then exposed to ultraviolet light. If a positive resist is used, the exposed portion of the first photoresist layer 102 is in the desired stent pattern. The portion of the photoresist that is exposed to light becomes soluble to the photoresist developer. After exposure, the resist coated substrate 100 is immersed in a developing solution, which dissolves the exposed areas. If a negative resist is used, the masked portion of the photoresist layer is in the desired stent pattern. With the mask in place, the photoresist layer is exposed to an ultraviolet light source and the photoresist beneath the clear areas of the mask undergoes a physical and chemical change that renders it insoluble in the developing solution. After exposure, the resist coated substrate 100 is immersed in the developing solution, which allows the unexposed areas to be removed without excessive effect on the hardened or exposed area. As shown in FIGS. 3 and 3A the stent pattern is defined by the openings 104 in the first photoresist layer 102, that is, the area of the photoresist that is removed, thus exposing the substrate 100.

After the photoresist layer 102 has been patterned, inner strut layer 106 is plated onto the substrate 100. Inner strut layer 106 may be made of stainless steel, a cobalt-chromium alloy, nickel, a nickel-cobalt alloy, a nickel-iron alloy, an iron-cobalt-nickel alloy, a chromium-iron-nickel alloy, and other metals or alloys known to those of ordinary skill in the art. Inner strut layer 106 may be formed by electro-forming a chemical composition of the metal or alloy of inner strut layer 106. The substrate 100 is placed in a metal plating bath of the metal or alloy and a current is run through the exposed areas 104 of the substrate 100, thereby causing the metal or alloy to build up in the openings 104. Inner strut layer 106 may be in the range of about 25 to 50 microns in thickness.

In the next step, the photoresist layer 102 is removed, leaving the substrate 100 and the inner strut layer 106, as shown in FIG. 5. Openings 108 are disposed between portions of the inner strut layer 106 where the first photoresist layer 102 was disposed, thereby exposing substrate 100, as shown in FIGS. 5 and 5A. First photoresist layer 102 may be removed by methods known to those of ordinary skill in the art. For example, and not by way of limitation, first photoresist layer may be removed by: 1) solvent dissolution of resist; 2) plasma oxygen stripping and aqueous rinsing; or 3) flood exposure and development of patterned resist (for positive resists and non hardened resist patterns).

After the first photoresist layer 102 is removed, a second photoresist layer 110 is applied, coating the inner strut layer 106 and the openings 108 disposed therebetween, as shown in FIG. 6. The second photoresist layer 110 may be the same material as the first photoresist layer 102, or may be a different material. The second photoresist layer 110 may be applied in the same manners described above with respect to the first photoresist layer 102. Second photoresist lay 110 may be in the range of 10-100 microns thick (typically 10-25 microns). Further, second photoresist layer 110 may be applied without first removing first photoresist layer 102. In such a situation, first photoresist layer 102 and second photoresist layer 110 will both be removed in a later step. However, in such a situation, cleaning first photoresist layer 102 may be more difficult in a later step due to drying processing for each layer.

The second photoresist layer 110 is then patterned. As shown in FIG. 7, the patterning of second photoresist layer 110 creates openings 112 over a portion of inner strut layer 106. The second photoresist layer 110 may be patterned as described above with respect to the first photoresist layer 102, or by other methods known to those of ordinary skill in the art. The openings 112 are sized for the desired size of the cavities in the struts of the stent.

After the second photoresist layer 110 has been patterned, a sacrificial layer 114 is deposited in openings 112 of second photoresist layer 110. Sacrificial layer 114 may be made of the same material as substrate 100 (or the coating layer of substrate 100), such as copper, or of other materials that may be removed after the top strut layer is deposited, as described in more detail below. Sacrificial layer 114 is sized for the desired size of the cavity or lumen within the struts of the stent.

Figure 9:
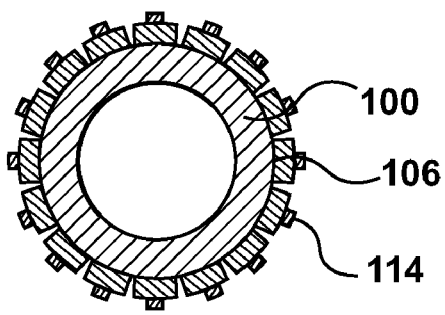
FIG. 9 is a cross-sectional view showing that the remaining second photoresist layer of FIG. 8 has been removed.

The second photoresist layer 110 is then removed, leaving the substrate 100, the inner strut layer 106 disposed on the substrate 100, and the sacrificial layer 114 disposed on portions of the inner strut layer 106, as shown in FIG. 9. The second photoresist layer 110 may be removed using the same methods described above with respect to removal of the first photoresist layer 102, or other methods known to those of ordinary skill in the art.

Figure 10:
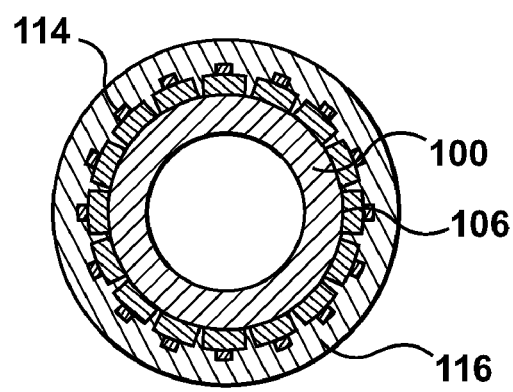
FIG. 10 is a cross-sectional view showing a third photoresist layer deposited over the substrate, first strut layer, and sacrificial material of FIG. 9.

After the second photoresist layer 110 is removed, a third photoresist layer 116 is deposited over the sacrificial layer 114, first strut layer 106, and substrate 100, as shown in FIG. 10. Similarly to the second photoresist layer 110 being applied over the first photoresist layer 102, third photoresist layer 116 may be applied over second photoresist layer 110 without prior removal of second photoresist layer 110. However, as also noted above, later processes for removing accumulated photoresist layers may be more difficult. The third photoresist layer 116 may be deposited by the methods described above with respect to the first photoresist layer 102, or other methods known to those of ordinary skill in the art.

Figure 11:
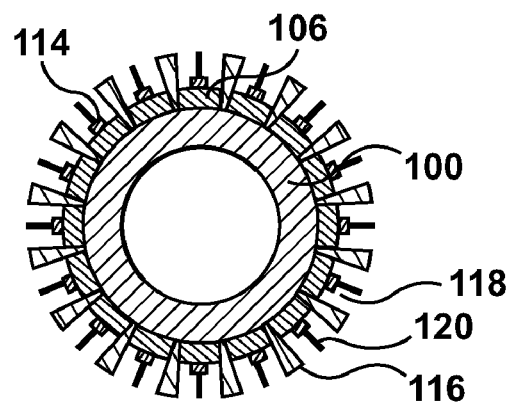
FIG. 11 is a cross-sectional view showing patterning of the third photoresist layer of FIG. 10.

After the third photoresist layer 116 is deposited, the third photoresist layer 116 is patterned. The third photoresist layer 116 may be patterned by any of the methods described above for patterning the first photoresist layer 102, or other methods known to those of ordinary skill in the art. As shown in FIG. 11, the pattern for the third photoresist layer 116 provides openings 118 for the second layer of strut material, described below. As also shown in FIG. 11, portions 120 of third photoresist layer 116 remain on sacrificial material 114. Portions 120 provide openings through the strut material to provide access the strut cavities, as described in more detail below.

Figure 12:
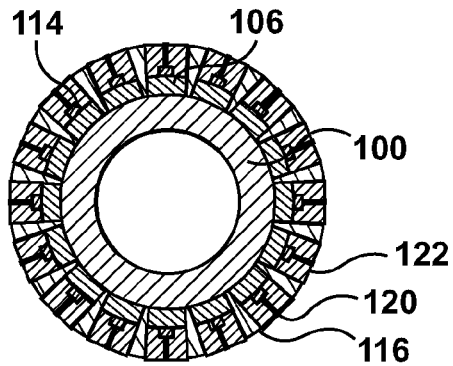
FIG. 12 is a cross-sectional view showing a second strut layer deposited in the openings of the patterned third photoresist layer of FIG. 11.
Figure 13:
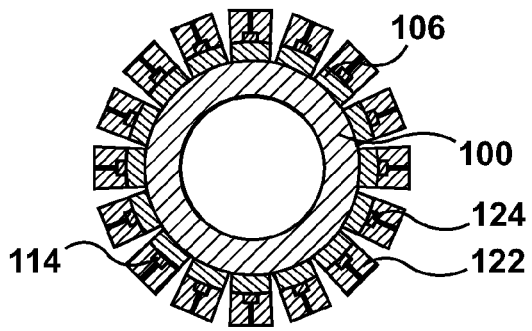
FIG. 13 is a cross-sectional view showing that the remaining third photoresist layer of FIG. 12 has been removed.

After the third photoresist layer 116 is patterned, a second strut layer 122 is deposited in the openings 118 of the third photoresist layer 116. Second strut layer 122 is preferably made of the same material as inner strut layer 106. Second strut layer 122 is formed in the openings 118 of third photoresist layer 116, as shown in FIG. 12. As can be seen in FIG. 12, second strut layer 122 is formed over portions of the inner strut layer 106 and along the sides of and over portions of the top of the sacrificial material 114. Second strut layer 122 may be formed by the same methods described above with respect to the inner strut layer 106. Second strut layer 106 provides the side walls and outer wall of the struts of the stent.

After the second strut layer 122 is formed, the remaining portions of the third photoresist layer 116 are removed. Third photoresist layer 116 may be removed using the same methods described above for removing the first photoresist layer 102, or any other methods known to those of ordinary skill in the art. After the third photoresist layer 116 is removed, the inner strut layer 106 and second strut layer 122 remain disposed on substrate 100, with sacrificial material 114 remaining in the cavities between the strut layers 106/122, as shown in FIG. 13.

The sacrificial material 114 and substrate 100 may then be removed, for example, by chemical etching, or other methods known to those of ordinary skill in the art. The removal of sacrificial material 114 and substrate 100 is accomplished without damaging strut layers 122, 106. For example, and not by way of limitation, if substrate 100 and sacrificial material 114 are copper or silver, they may be removed using nitric acid. If iron, zinc or magnesium is used for substrate 100 and/or sacrificial material 114, then hydrochloric acid may be used for removal. Phosphoric acid mixtures may be used to remove sacrificial layers made from aluminum. Gas or plasma etching may be used to removed sacrificial layer made from tungsten, molybdenum, tantalum or carbon. As would be understood by those of ordinary skill in the art, various materials can be used for the sacrificial material 114 and substrate 100, and various materials can be used for strut layers 122, 106. The materials and etchants are selected such that the etchants dissolve or otherwise remove the cavity and substrate sacrificial materials 114, 100 without damaging the strut layer materials 122, 106. U.S. application Ser. No. 12/500,359, filed Jul. 9, 2009, incorporated herein in its entirety by reference, discloses various etchants that remove one metal or alloy without damaging another metal or alloy. Further, those of ordinary skill in the art would recognize that substrate 100 may only include a surface coating of the sacrificial material. In such an embodiment, removal of the surface coating reduces the outer diameter of the substrate 100 sufficiently such that the stent 130 may be removed therefrom.

Figure 14:
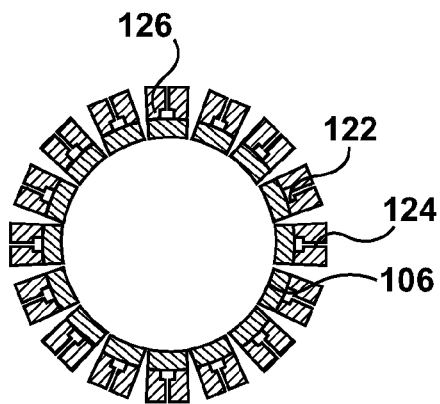
FIG. 14 is a cross-sectional view showing that the substrate and sacrificial material of FIG. 13 has been removed.
Figure 14A:
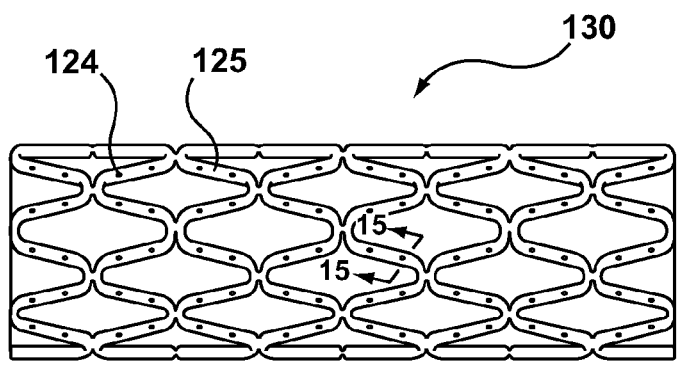
FIG. 14A is a schematic side view of a stent.
Figure 15:
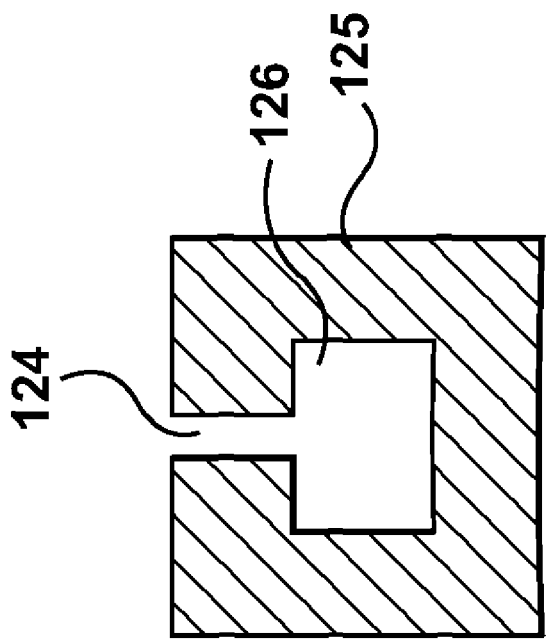
FIG. 15 is a cross-sectional view taken along line 15-15 of FIG. 14A.

Upon removal of the sacrificial material 114 and substrate 100, the strut layers 106, 122 remain as struts 125 of stent 130, as shown in FIGS. 14 and 14A. The struts 125 include a cavity 126 and an opening 124 from the cavity 126 to an outer surface of the strut 125, as shown in FIG. 15.

Figure 16:
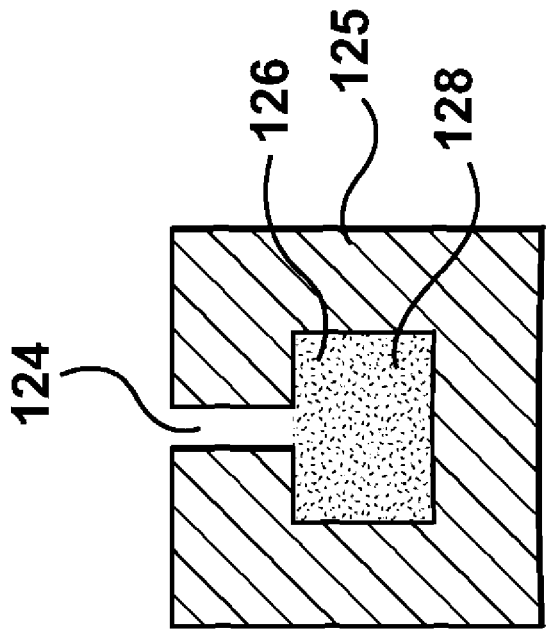
FIG. 16 is the portion of the strut of FIG. 15 showing a therapeutic substance deposited in the cavity.

The cavity 126 may then be filled with a therapeutic substance 128, as shown in FIG. 16. Cavity 126 may be filled through openings 124 and/or other openings created for the purpose of filling cavity 126. Such additional openings, if used, may then be closed after cavity 126 is filled with the therapeutic substance 128. Cavity 126 may be filled with the therapeutic substance by methods known to those of ordinary skill in the art. Cavity 126 may be filled, for example, by flowing a liquid or semi-liquid state of the therapeutic agent through the openings 124 or other openings provided.

It would be understood by those of ordinary skill in the art that cavities 126 in struts 125 may be continuous such that there is essentially one cavity 126 extending within the struts 125, with openings 124 located at various locations along the struts. However, by altering the pattern for the photoresist layers, in particular, second and third photoresist layers 110/116, the cavities 126 need not be continuous. For example, and not by way of limitation, at certain locations, some openings 112 in second photoresist layer 110 may not be included such that second photoresist layer 110 remains at these locations. Thus, sacrificial material 114 would not be added at these locations, and portions 120 of third photoresist layer 116 at these locations would be removed. Thus, at these locations, second strut layer 122 would completely cover first strut layer 106 such that there is no cavity 124 at these locations. For example, and not by way of limitation, a solid strut may be provided near each end of the stent. Thus, a first therapeutic substance could be used at the ends of the stent and a second therapeutic substance could be used in the middle portion of the stent. Alternatively, portions of the stent that are subject to higher loads during delivery or expansion may include solid struts in order to provide better load bearing. Those of ordinary skill in the art would understand that with the methods described herein, endless possibilities exist for patterning the photoresist layers to divide the cavities 126 into as many discrete cavities as desired, or to have a single, continuous cavity along the length of the entire strut.

It would further be understood that openings 124 are preferably not continuous. Instead, openings 124 are located at different locations along strut 125, as shown in FIG. 14A. However, those of ordinary skill in the art would recognize that openings 124 may be continuous. Further, by altering the patterning of the photoresist layers, the size, shape, and/or density (number per unit length or area) of the openings 124 may be varied along the stent. Such variations may alter the elution rate of the therapeutic substance along the stent. For example, and not by way of limitation, more or larger openings may be providing in the middle portion of the stent and less or smaller openings may be provided near the ends of the stent.

The therapeutic substance 128 may include, but is not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include nitric oxide, alpha-interferon, genetically engineered epithelial cells, and dexamethasone. In other examples, the therapeutic substance is a radioactive isotope for implantable device usage in radiotherapeutic procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

Further, a carrier may be used with the therapeutic substance or drug. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the drug and the solvent to aid elution of the drug.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of making a stent including hollow struts comprising the steps of:
    utilizing a substantially cylindrical substrate at least partially made from a sacrificial material;
    depositing a first photoresist layer on the substrate;
    patterning the first photoresist layer to provide openings in the first photoresist layer;
    depositing a first metal layer on the substrate in the openings of the patterned first photoresist layer;
    depositing a second photoresist layer over the first metal layer;
    patterning the second photoresist layer to provide openings in the second photoresist layer, wherein the openings in the second photoresist layer are provided over the first metal layer;
    depositing a sacrificial material on the first metal layer in the openings of the second patterned photoresist layer;
    depositing a third photoresist layer over the sacrificial material and the first metal layer;
    patterning the third photoresist layer to provide openings in the third photoresist layer;
    depositing a second metal layer in the openings of the patterned third photoresist layer;
    removing the first, second and third photoresist layers; and
    removing the substrate and the sacrificial material.

2. The method of claim 1, wherein the step of removing the first photoresist layer is completed before the step of depositing the second photoresist layer.

3. The method of claim 2, wherein the step of removing the second photoresist layer is completed before the step of depositing the third photoresist layer.

4. The method of claim 1, wherein the first metal layer and the second metal layer are the same material.

5. The method of claim 1, wherein the first metal layer and the second metal layer are selected from the group consisting of stainless steel, a cobalt-chromium alloy, nickel, a nickel-cobalt alloy, a nickel-iron alloy, an iron-cobalt-nickel alloy, and a chromium-iron-nickel alloy.

6. The method of claim 1, wherein the step of depositing the first metal layer comprises electro-forming a chemical composition of the metal onto the substrate.

7. The method of claim 6, wherein the step of electro-forming comprises placing the substrate in a metal plating bath of the metal and running a current through the substrate to cause the metal build up in the openings of the patterned first photoresist layer.

8. The method of claim 1, wherein the steps of removing the first, second and third photoresist layers comprises one of solvent dissolution of resist, plasma oxygen stripping and aqueous rinsing, and flood exposure and development of patterned resist.

9. The method of claim 1, wherein the first metal layer and second metal layer form the struts of the stent.

10. The method of claim 9, wherein the removed sacrificial material forms a cavity with the struts of the stent.

11. The method of claim 10, wherein the step of patterning the third photoresist layer comprises leaving a portions of the third photoresist layer over portions of the sacrificial material to form openings from the cavity through the second metal layer.

12. The method of claim 10, further comprising the step of filling the cavity with a therapeutic substance.

* * * * *